US00PP14480P29

(12) United States Plant Patent
Morris

(10) Patent No.: US PP14,480 P2
(45) Date of Patent: Jan. 20, 2004

(54) MINT PLANT NAMED 'MCKENZIE'

(50) Latin Name: *Mentha×piperita*
Varietal Denomination: McKenzie

(75) Inventor: Mark Morris, Eugene, OR (US)

(73) Assignee: A. M. Todd Company, Kalamazoo, MI (US)

( * ) Notice: Subject to any disclaimer, the term of this patent is extended or adjusted under 35 U.S.C. 154(b) by 0 days.

(21) Appl. No.: 10/193,191

(22) Filed: Jul. 12, 2002

(51) Int. Cl.[7] ..... A01H 5/00

(52) U.S. Cl. ..... Plt./259

(58) Field of Search ..... Plt./259, 258

*Primary Examiner*—Bruce R. Campell
*Assistant Examiner*—June Hwu
(74) *Attorney, Agent, or Firm*—Kramer & Amado, P.C.

(57) ABSTRACT

A new and distinct peppermint plant 'McKenzie' characterized by its upright growth habit, vigorous and abundant root growth, resistance to Spider Mites (*Tetranychus urticae*), Mint rust (*Puccinia menthe* Pers), Mint wilt (*Verticillium dahliae* and *Verticillium albo-atrum*), and a distinct flower spike with mostly pinkish white petals and consistent oil quality throughout its phases of maturity.

3 Drawing Sheets

Latin name of the genus and species of the plant claimed: *Mentha×piperita.*

Variety denomination: 'McKenzie'.

FIELD OF THE INVENTION

The present invention relates to a new and distinct peppermint plant botanically known as *Mentha×piperita*. The new variety has been named 'McKenzie' and will be referred as such hereafter.

BACKGROUND OF THE INVENTION

The new peppermint plant of the present invention was developed in an effort to cultivate a peppermint variety exhibiting an upright growth habit, vigorous and abundant root growth, greater resistance to Spider mites (*Tetranychus urticae*), Mint rust (*Puccinia menthe* Pers) and *Verticillium wilt* (*Verticillium dahliae* and *V. albo-atrum*). Further, 'McKenzie' produces a peppermint oil that varies minimally in oil profile based on plant maturity.

The inventor explored ways of creating peppermint hybrids through conventional crosses from the 'Black Mitcham' (*Mentha piperita*)—not-patented—parent plants without the use of chemicals to increase ploidy. The method relied on adjusting environmental conditions to generate viable pollen. Using this method, several seedlings were generated in 1996 using two 'Black Mitcham' peppermint plants as parents.

The resulting selection has been under continuous evaluation at the A. M. Todd facility located in Jefferson, Oreg., since 1996 and has been asexually propagated through stem, propagules and rhizome cuttings. The resulting propagules have remained identical to the parent plant in appearance, resistance to the common diseases encountered by mint plants, peppermint oil quality and vigorous root growth.

SUMMARY OF THE INVENTION

The present invention relates to a novel peppermint plant named 'McKenzie' characterized by its more upright growth habit as shown by taller growth with thicker stems, when compared to commercial peppermint varieties, more abundant and vigorous root growth and resistance to Mint rust (*Puccinia menthe* Pers), *Verticillium wilt* (*Verticillium dahliae* and *V. albo-atrum*), and Spider mites (*Tetranychus urticae*). The peppermint oil profile of 'McKenzie' is also similar throughout its maturity when grown in Oregon and Washington.

BRIEF DESCRIPTION OF THE PHOTOGRAPHS

Figure 1:
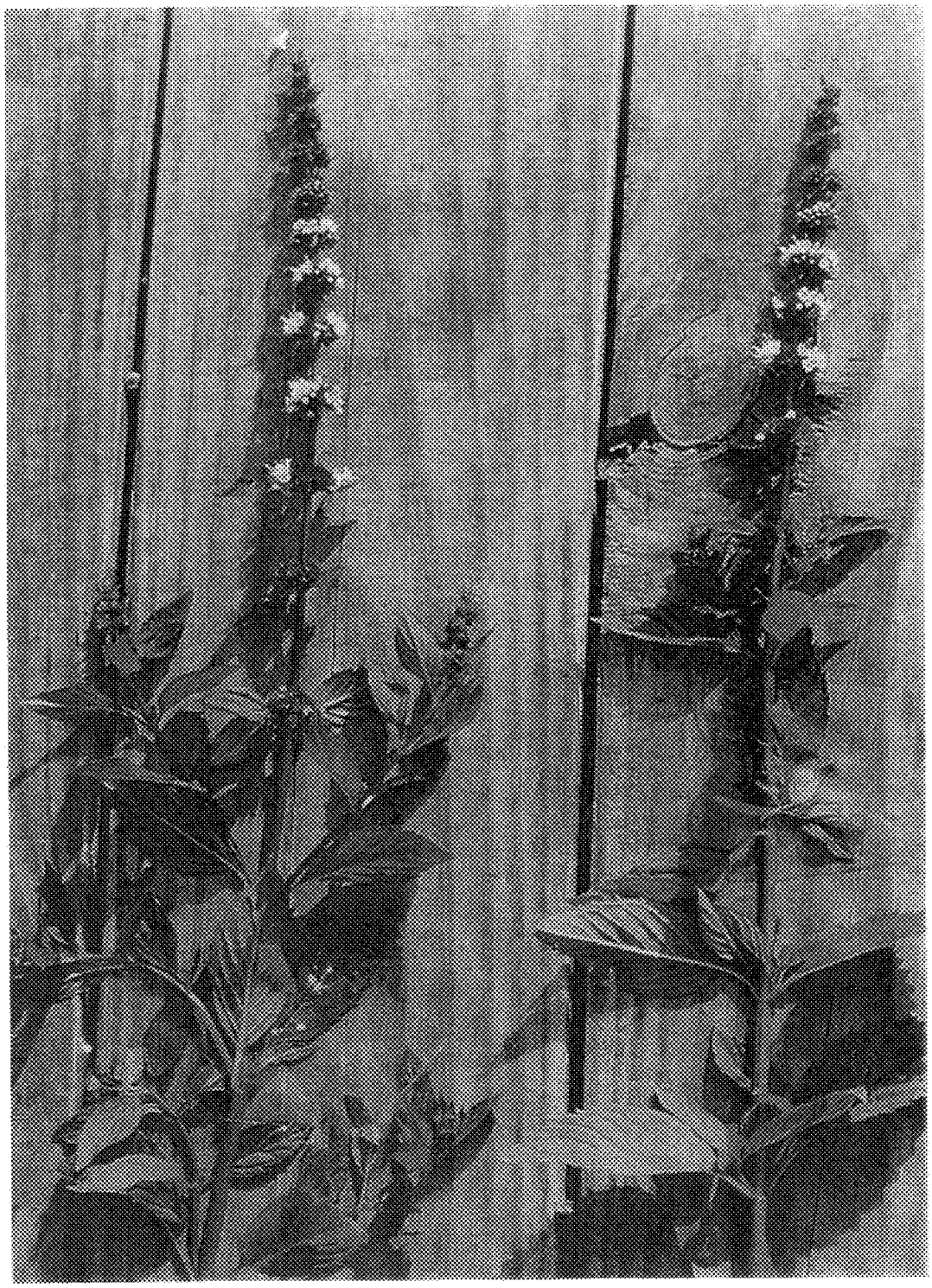

The accompanying color photographs of 'McKenzie' show the new variety:

FIG. 1: shows cuttings of the claimed plant 'McKenzie' including its foliage and inflorescences.

Figure 2:
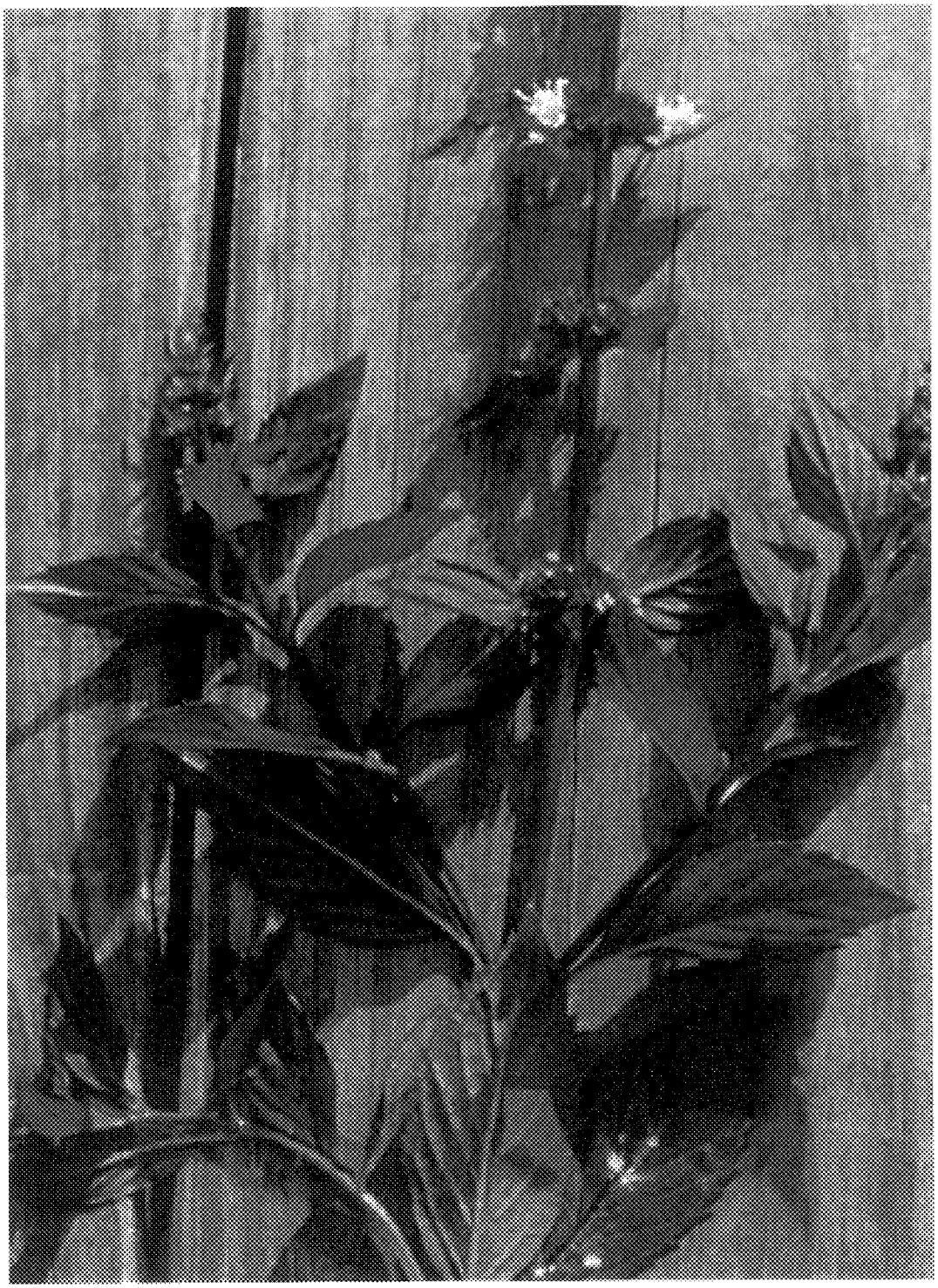

FIG. 2: shows the mature leaves of 'McKenzie'.

Figure 3:
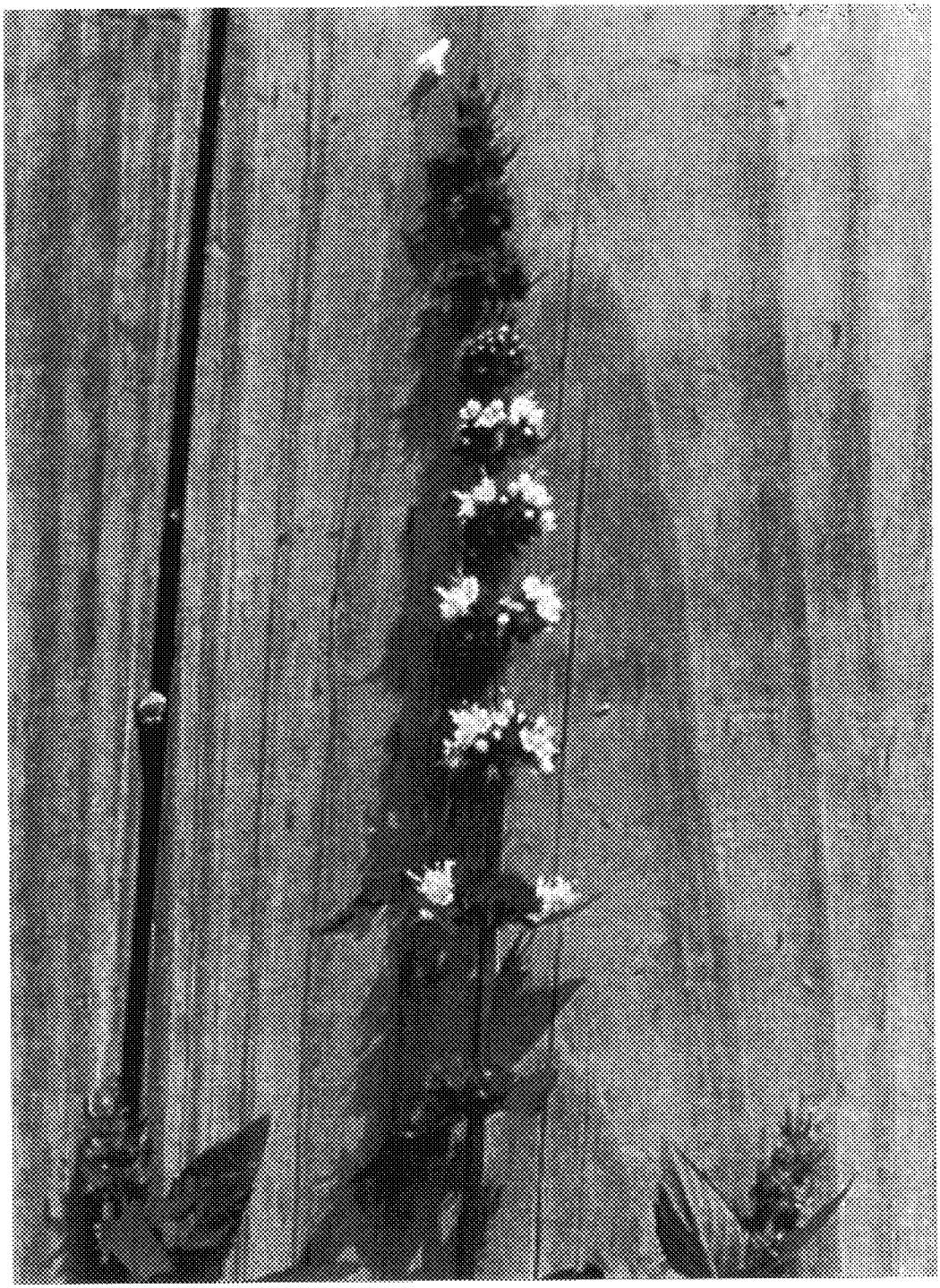

FIG. 3: shows the flower spike of 'McKenzie' and its flower whorls having mostly pinkish-white flower petals.

DETAILED DESCRIPTION OF THE INVENTION

The present invention is a new and distinct variety of peppermint plant having the following characteristics that, in combination, are not exhibited in other peppermint plants:

1. More upright growth habit;
2. More vigorous and abundant root growth;
3. Improved resistance to Spider mites (*Tetranychus urticae*);
4. Oil profile that shows little variability based on plant maturity.
5. Improved resistance to Mint rust (*Puccinia menthe* Pers);
6. Improved resistance to *Verticillium wilt* (*Verticillium dahliae* and *V. albo-artum*).

'McKenzie' is an herbaceous perennial with an upright shrubby growth habit. This facilitates harvesting and thereby reduces costs. The observed plants were two years old and were grown outdoors in western Oregon, in a silt-loam soil. Based on an initial May planting density of 8,000 plants per acre, a new 'McKenzie' rootstock field fills in by mid-June. The density of rhizomes from this acre of rootstock allows for a 15 to 1 expansion the following year compared to 10 to 1 for 'Black Mitcham.' Numerous branching stems are produced each year with an eventual height between 70–90 cm. The approximate plant spread is in the range of 14–24 cm reflecting a size measurement half way up the plant during bloom on a managed field plot. Measurements taken at different times of the year, on different locations of the plants, under different crop management regimes will vary. As 'McKenzie' is a rhizomatous perennial; it is not possible to specify the accurate dimensions of one single plant because the differentiation of where one plant terminates and another begins is unknown. At the end of one growing season, it is estimated that one rooted cutting will have spread through a six square foot area. When compared to 'Black Mitcham', the industry standard, which is not patented and has been commercially grown for hundreds or years, 'McKenzie' is more upright in its growth habit, taller with thicker stems (due to a large extent to the highly lignified stems which reduces lodging), larger leaves and a lighter green color with less anthocyanin pigment development under similar growing conditions.

'McKenzie' has a square stem, in the range of 6 mm on a side, compared to the average 4.5 mm stem of 'Black Mitcham.' Stems and leaves, especially along leaf veins, are sparsely pubescent, more so than 'Black Mitcham.' This increased stem thickness results in reduced field lodging and a stronger overall stem. Based on flowering 'McKenzie' matures at approximately the same time as 'Black Mitcham.' 'McKenzie' also features the additional benefit of vigorous and abundant root growth, which results in more rapid acreage expansion and reduction in planting costs. As compared to the peppermint plant 'Clackamas', which is disclosed in co-pending application No. 10/193,213, 'McKenzie' has a substantially elongated flower spike, thicker stems, darker leaf color and, on average a taller growth habit with larger leaves.

All color descriptions according The R.H.S. Colour Chart. In botanical terms, 'McKenzie' has a distinct flower spike that is quite elongated as compared to other peppermints and can be up to 30 cm long under some growing conditions when measured from the lowermost verticillaster to the tip. The number of paired flower whorls, or verticillasters, can vary from 8 to 20. The first internode between verticiels varies from 1.8 to 4.0 cm. Flower petal color is much lighter than 'Black Mitcham'. The petals are mostly pinkish-white, but have a very slight lavender cast to them. The leaves half way up the main stem are approximately 7.5 cm long by 2.4 cm wide and have an ovate shape with a serrate margin. The leaves are oppositely arranged on the stem with an equilateral base, an acute apex, and serrate margin. Ventral leaf surface color is 139A (Green Group), dorsal color is 137B (Green Group), petiole color is 147C (Yellow-green Group). Stem color is 146C (Yellow-Green Group) near the base and gradually becomes more purple until the color at the apex is 187A (Greyed-Purple Group). The fragrance is peppermint-like.

The flowers of 'McKenzie' contain a 4-lobed, nearly regular corolla 73D (Red-purple Group) with a short tube, 8 mm long from the base of the calyx to the tip of the forked white stigma. The calyx generally has an average of five ciliate teeth fused at the base forming a short tube and is 4 mm long. The calyx, peduncle and pedicel colors are 187A (Greyed-purple Group). Each flower has one pistil with a 7 mm long white style and four epipetalous stamens that may be exerted with 4 mm long white filaments. The white anthers are less that 1 mm. Pollen color is 10D (Yellow Group). The formation of seed is a rare event. There is no obvious flower fragrance and the plant does not produce fruit or seed.

The oil produced by 'McKenzie' is of a typical peppermint type. In contrast to 'Black Mitcham', the oil profile of the 'McKenzie' varies little with plant maturity. This feature allows for increased yield due to flexible harvest timing during a single season without significant changes occurring to its oil profile. 'McKenzie' has an herbage yield of approximately 70 lbs./acre and an essential oil quality of peppermint oil having a 10 to 20 percent higher menthol content than standard 'Black Mitcham' peppermint.

'McKenzie' has been grown and observed under 3 different field conditions as well as under greenhouse conditions. As with all plants, the traits have varied depending on location. These differences can be attributed to varying climates, soils, fertilizers and water regimes. However, 'McKenzie' remains distinct from other peppermint plants in its characteristics. The resistance to the diseases identified above is presented in Table I. The results were gathered from a study performed in western Oregon and show the comparison of 'McKenzie' to 'Black Mitcham' according to the mean number of rust pustules per leaf, mean number of Verticillium strikes per plot and mean number of spider mites per leaf during three years of analysis.

TABLE 1

| | Mean Number of Rust Pistules per leaf | Mean Number of Verticillium strikes per plot | Mean Number of Spider Mites per leaf |
|---|---|---|---|
| Aug. 15, 1999 | | | |
| 'MCKENZIE' | 0.00 | 0.00 | 0.75 |
| 'Black Mitchum' | 40.30 | 9.25 | 8.25 |
| Aug. 22, 2000 | | | |
| 'MCKENZIE' | 0.00 | 0.75 | 0.58 |
| 'Black Mitchum' | 183.25 | 17.00 | 10.00 |
| Aug. 26, 2001 | | | |
| 'MCKENZIE' | 0.25 | 1.75 | 0.25 |
| 'Black Mitchum' | 81.25 | 30.50 | 11.25 |

As illustrated by Table I, 'McKenzie' is significantly more resistant to the diseases shown. For example, although the incidence of Mint Rust varied overall according to the three years shown due to differences in annual growing conditions, 'McKenzie' consistently showed much greater resistance to *Puccinia menthe* Pers when compared to the mean number of Rust Pustules per leaf. In fact, Mint Rust was almost eliminated. Similarly, the number of mean strikes per plot for *Verticillium dahliae* and *Verticillium albo-atrum* was markedly reduced by 'McKenzie' when compared to 'Black Mitcham.' In the case of *Tetranychus urticae*, the man number of Spider Mites per leaf was, again, almost eliminated in comparison to 'Black Mitcham'.

While the plant identified in the present invention has been described as it relates to a specific embodiment, it is understood that this application is intended to cover other variations, uses and adaptations that may arise under different environmental conditions.

What is claimed is:

1. A new and distinct variety of peppermint plant, substantially as shown and described.

* * * * *